United States Patent
Palti

(10) Patent No.: US 7,599,746 B2
(45) Date of Patent: *Oct. 6, 2009

(54) APPARATUS AND METHOD FOR PREVENTING THE SPREAD OF CANCEROUS METASTASES AND FOR ELIMINATION OF METASTASES

(75) Inventor: Yoram Palti, Haifa (IL)

(73) Assignee: Standen Ltd, St. Helier (JE)

( * ) Notice: Subject to any disclaimer, the term of this patent is extended or adjusted under 35 U.S.C. 154(b) by 230 days.

This patent is subject to a terminal disclaimer.

(21) Appl. No.: 11/422,641

(22) Filed: Jun. 7, 2006

(65) Prior Publication Data

US 2006/0276858 A1    Dec. 7, 2006

Related U.S. Application Data

(63) Continuation-in-part of application No. 11/111,393, filed on Apr. 21, 2005, which is a continuation-in-part of application No. 11/074,318, filed on Mar. 7, 2005, which is a continuation-in-part of application No. 10/315,576, filed on Dec. 10, 2002, now Pat. No. 6,868,289, which is a continuation-in-part of application No. 10/285,313, filed on Oct. 31, 2002, now Pat. No. 7,089,054, which is a continuation-in-part of application No. 10/263,329, filed on Oct. 2, 2002, now Pat. No. 7,136,699, said application No. 11/111,393 is a continuation-in-part of application No. 10/402,327, filed on Mar. 28, 2003, now Pat. No. 7,146,210, which is a continuation-in-part of application No. 10/204,334, filed as application No. PCT/IB01/00202 on Feb. 16, 2001, now Pat. No. 7,333,852, said application No. 11/111,393 is a continuation-in-part of application No. 10/288,562, filed on Nov. 5, 2002, now Pat. No. 7,016,725.

(60) Provisional application No. 60/689,013, filed on Jun. 8, 2005, provisional application No. 60/565,065, filed on Apr. 23, 2004, provisional application No. 60/183,295, filed on Feb. 17, 2000, provisional application No. 60/338,632, filed on Nov. 6, 2001.

(51) Int. Cl.
*A61N 1/00* (2006.01)

(52) U.S. Cl. ...................................................... 607/76

(58) Field of Classification Search .................. 607/76, 607/2; 604/20, 114; 128/898
See application file for complete search history.

(56) References Cited

U.S. PATENT DOCUMENTS 2,220,269 A    11/1940    Patzold et al.

(Continued)

FOREIGN PATENT DOCUMENTS

EP    0 330 797 A2    9/1989

(Continued)

OTHER PUBLICATIONS

Hofmann et al., "Electronic Genetic-Physical and Biological Aspects of Cellular Electomanipulation", IEEE Eng. in Med. and Biology Mag., Dec. 1986, p. 6-23, New York.

(Continued)

*Primary Examiner*—George Manuel
(74) *Attorney, Agent, or Firm*—Proskauer Rose LLP

(57) ABSTRACT

AC electric fields at certain frequencies and field strengths disrupt dividing cells, but leave undividing cells substantially unharmed. Since cancer cells divide much more often than normal cells, those AC fields have been shown to be effective at inhibiting tumor growth and shrinking tumors. Because certain body parts (e.g., the lungs and the liver) are at high risk for developing metastases in patients with some forms of cancer, treating those body parts with those AC fields can prevent metastases from growing in those body parts. This treatment may be used both after a metastasis has reached a detectable size and prophylactically (to prevent such metastases from ever reaching a detectable size in the first place). It may also be used to prevent cancer in people with a high probability of developing cancer (e.g., based on family history).

26 Claims, 3 Drawing Sheets

U.S. PATENT DOCUMENTS

| | | | |
|---|---|---|---|
| 4,016,886 A | 4/1977 | Doss et al. | |
| 4,121,592 A | 10/1978 | Whalley | |
| 4,263,920 A | 4/1981 | Tasto et al. | |
| 4,467,809 A | 8/1984 | Brighton | |
| 4,472,506 A | 9/1984 | Liburdy | |
| 4,622,952 A | 11/1986 | Gordon | |
| 4,626,506 A | 12/1986 | Zimmermann et al. | |
| 4,676,258 A | 6/1987 | Inokuchi et al. | |
| 4,822,470 A | 4/1989 | Chang | |
| 4,846,178 A | 7/1989 | Fuxue et al. | |
| 4,846,196 A | 7/1989 | Wiksell et al. | |
| 4,923,814 A | 5/1990 | Marshall | |
| 4,936,303 A | 6/1990 | Derwiler et al. | |
| 4,971,991 A | 11/1990 | Umemura et al. | |
| 5,099,756 A | 3/1992 | Franconi et al. | |
| 5,158,071 A | 10/1992 | Umemura et al. | |
| 5,236,410 A | 8/1993 | Granov et al. | |
| 5,269,304 A | 12/1993 | Matthews | |
| 5,312,813 A | 5/1994 | Costerton et al. | |
| 5,386,837 A | 2/1995 | Sterzer | |
| 5,389,069 A | 2/1995 | Weaver | |
| 5,441,532 A | 8/1995 | Fenn | |
| 5,441,746 A | 8/1995 | Chagnon | |
| 5,468,223 A | 11/1995 | Mir | |
| 5,606,971 A | 3/1997 | Sarvazyn | |
| 5,674,267 A | 10/1997 | Mir et al. | |
| 5,683,366 A * | 11/1997 | Eggers et al. | 604/114 |
| 5,718,246 A | 2/1998 | Vona | |
| 5,807,257 A | 9/1998 | Bridges | |
| 5,964,726 A | 10/1999 | Korenstein et al. | |
| 5,976,092 A | 11/1999 | Chinn | |
| 5,984,882 A | 11/1999 | Rosenschein et al. | |
| 6,027,488 A | 2/2000 | Hofmann et al. | |
| 6,043,066 A | 3/2000 | Mangano et al. | |
| 6,055,453 A | 4/2000 | Hofmann et al. | |
| 6,068,650 A | 5/2000 | Hofmann et al. | |
| 6,096,020 A | 8/2000 | Hofmann et al. | |
| 6,319,901 B1 | 11/2001 | Bernard et al. | |
| 6,366,808 B1 | 4/2002 | Schroeppel et al. | |
| 6,413,255 B1 | 7/2002 | Stern | |
| 6,447,499 B2 | 9/2002 | Gray | |
| 6,856,839 B2 | 2/2005 | Litovitz | |
| 2002/0193832 A1 | 12/2002 | Gray | |
| 2002/0193833 A1 | 12/2002 | Dimmer et al. | |
| 2003/0060856 A1 | 3/2003 | Chornenky et al. | |
| 2003/0191506 A1 | 10/2003 | Shloznikov | |
| 2005/0209640 A1 | 9/2005 | Palti | |
| 2005/0209642 A1 | 9/2005 | Palti | |
| 2006/0149341 A1 | 7/2006 | Palti | |
| 2006/0167499 A1 | 7/2006 | Palti | |

FOREIGN PATENT DOCUMENTS

| | | |
|---|---|---|
| GB | 1 419 660 A1 | 12/1975 |
| GB | 2 026 322 A1 | 2/1980 |
| GB | 2 043 453 A1 | 10/1980 |
| WO | WO 01/60994 | 8/2001 |

OTHER PUBLICATIONS

Berg et al., "Electric Field Effects on Bilogical Membranes:Electoincorporation and Electofusion",Ettore Maj Inter. Science, 1987,p. 135-166,vol. 32,Phys. Science, New York.

Kirson et al., "Disruption of Cancer Cell Replication by Alternating Electric Fields", Cancer Research 64, May 2004, p. 3288-3295, Haifa, Israel.

Asbury et al., "Trapping of DNA in Nonuniform Oscillating Electric Fields", Biophysical Journal, Feb. 1998, p. 1024-1030, vol. 74,Seattle, WA.

* cited by examiner

APPARATUS AND METHOD FOR PREVENTING THE SPREAD OF CANCEROUS METASTASES AND FOR ELIMINATION OF METASTASES

CROSS REFERENCE TO RELATED APPLICATIONS

This application claims priority to U.S. provisional application No. 60/689,013, filed Jun. 8, 2005; this application is also a continuation-in-part of application Ser. No. 11/111,393 filed Apr. 21, 2005, which (a) claims the benefit of U.S. provisional application 60/565,065, filed Apr. 23, 2004; (b) is a continuation-in-part of U.S. patent application Ser. No. 11/074,318, filed Mar. 7, 2005, which is a continuation-in-part of U.S. patent application Ser. No. 10/315,576, filed Dec. 10, 2002 (now U.S. Pat. No. 6,868,289), which is a continuation-in-part of U.S. patent application Ser. No. 10/285,313, filed Oct. 31, 2002, which is a continuation-in-part application of U.S. patent application Ser. No. 10/263,329, filed Oct. 2, 2002; (c) is a continuation-in-part of U.S. patent application Ser. No. 10/402,327, filed Mar. 28, 2003, which is a continuation-in-part of U.S. patent application Ser. No. 10/204,334, filed Oct. 16, 2002, which is the U.S. national phase of PCT/IB01/00202, filed Feb. 16, 2001, which claims the benefit of U.S. provisional application 60/183,295, filed Feb. 17, 2000; and (d) is a continuation-in-part of U.S. patent application Ser. No. 10/288,562, filed Nov. 5, 2002 (now U.S. Pat. No. 7,016,725), which claims the benefit of U.S. provisional application 60/338,632, filed Nov. 6, 2001. Each of the aforementioned applications is hereby incorporated by reference in its entirety.

BACKGROUND

This invention concerns the application of alternating electric fields and currents in patients or human subjects for the purpose of prevention of the formation of cancerous metastases and effecting or destroying metastases.

Living organisms proliferate by cell division, including tissues, cell cultures, microorganisms (such as bacteria, mycoplasma, yeast, protozoa, and other single-celled organisms), fungi, algae, plant cells, etc. Dividing cells of organisms can be destroyed, or their proliferation controlled, by methods that are based on the sensitivity of the dividing cells of these organisms to certain chemical or physical agents. For example, certain antibiotics stop the multiplication process of bacteria.

It is well known that tumors, particularly malignant or cancerous tumors, grow very uncontrollably compared to normal tissue. Such expedited growth enables tumors to occupy an ever-increasing space and to damage or destroy tissue adjacent thereto. Furthermore, certain cancers are characterized by an ability to spread metastases to new locations where the metastatic cancer cells grow into additional tumors.

The rapid growth of tumors and their metastases, in general, and malignant tumors in particular, as described above, is the result of relatively frequent cell division or multiplication of these cells compared to normal tissue cells. The distinguishably frequent cell division of cancer cells is the basis for the effectiveness of many existing cancer treatments, e.g., irradiation therapy and the use of various chemo-therapeutic agents. Such treatments are based on the fact that cells undergoing division are more sensitive to radiation and chemo-therapeutic agents than non-dividing cells. Because tumors cells divide much more frequently than normal cells, it is possible, to a certain extent, to selectively damage or destroy tumor cells by radiation therapy and/or chemotherapy. The actual sensitivity of cells to radiation, therapeutic agents, etc., is also dependent on specific characteristics of different types of normal or malignant cell types. Unfortunately, however, the sensitivity of tumor cells is not sufficiently higher than that of many types of normal tissues. This diminishes the ability to distinguish between tumor cells and normal cells, and therefore, existing cancer treatments typically cause significant damage to normal tissues, thus limiting the therapeutic effectiveness of such treatments. Also, certain types of tumors are not sensitive at all to existing methods of treatment.

Electric fields and currents have been used for medical purposes for many years. The most common is passing electric currents through portions of a human or animal body by application of an electric field using a pair of conductive electrodes between which a potential difference is maintained. These electric currents are used either to exert their specific effects, i.e., to stimulate excitable tissue, or to generate heat, since the body acts as a resistor. Examples of the first type of application include: cardiac defibrillators, peripheral nerve and muscle stimulators, brain stimulators, etc. Currents are used for heating, for example, in devices for tumor ablation, ablation of malfunctioning cardiac or brain tissue, cauterization, and relaxation of muscle rheumatic pain and other pain, etc.

Another use of electric fields for medical purposes involves the utilization of high frequency oscillating fields transmitted from a source that emits an electric wave, such as an RF wave or a microwave source, which is directed at the part of the body that is of interest (i.e., a target region). In these instances, no electric energy is transferred by conduction between the source and the body; but rather, the energy is transmitted to the body by radiation or induction. More specifically, the electric energy generated by the source reaches the vicinity of the body via a conductor and is transmitted from it through air or some other electric insulating material to the body.

Electric fields that can be used in medical applications can thus be separated generally into two different modes. In the first mode, the electric fields are applied to the body or tissues by means of conducting electrodes. These electric fields can be separated into two types, namely (1) steady fields or fields that change at relatively slow rates, and alternating fields of low frequencies that induce corresponding electric currents in the body or tissues, and (2) high frequency alternating fields (above 1 MHz) applied to the body by means of the conducting electrodes or by means of insulated electrodes.

The first type of electric field is used, for example, to stimulate nerves and muscles, pace the heart, etc. In fact, such fields are used in nature to propagate signals in nerve and muscle fibers, central nervous system (CNS), heart, etc. The recording of such natural fields is the basis for the ECG, EEG, EMG, ERG, etc. The field strength in conductive electrode applications, assuming a medium of homogenous electric properties, is simply the voltage difference applied to the stimulating/recording electrodes divided by the distance between them. The currents thus generated can be calculated by Ohm's law and can have dangerous stimulatory effects on the heart and CNS and can result in potentially harmful ion concentration changes. Also, if the currents are strong enough, they can cause excessive heating in the tissues. This heating can be calculated by the power dissipated in the tissue (the product of the voltage and the current).

When such electric fields and currents are alternating, their stimulatory power, on nerve, muscle, etc., is an inverse function of the frequency. At frequencies above 1-10 KHz, the stimulation power of fields approach zero. This limitation is due to the fact that excitation induced by electric stimulation is normally mediated by membrane potential changes, the rate of which is limited by the RC properties (time constraints on the order of 1 ms) of the membrane.

Regardless of the frequency, when such current inducing fields are applied, they are often associated with harmful side effects caused by currents. For example, one negative effect is the changes in ionic concentration in the various "compartments" within the system, and the harmful products of the electrolysis taking place at the surface of conducting electrodes and the release of toxic substances into the tissues or the medium in which the tissues are imbedded.

At one time, it was commonly believed that alternating fields of medium frequencies (about 50 kHz-1 MHz), had no biological effect except due to heating. Such fields can be applied to a conductive medium, such as a human body, via insulated electrodes. Under such conditions the electrodes induce in the body only capacitive currents. In contrast to the general belief that such fields have no direct biological effect, in U.S. patent applications Ser. Nos. 10/204,334 and 10/285, 313, and in U.S. Pat. Nos. 6,868,289 and 7,016,562, each of which is incorporated herein by reference, such fields, termed "TTFields," were shown to specifically target cancer cells for destruction. See also E. D. Kirson et al., *Disruption of Cancer Cell Replication by Alternating Electric Fields,* Cancer Research 64, 3288-3295, May 1, 2004, which is also incorporated herein by reference.

The present invention is designed to extend the use of TTFields to the prevention of the formation and elimination of established metastases as well as for the prevention of the development of cancers in subjects at risk.

SUMMARY

AC electric fields at certain frequencies and field strengths been shown to be effective at inhibiting tumor growth and shrinking tumors. Because certain body parts (e.g., the lungs and the liver) are at high risk for developing metastases in patients with some forms of cancer, treating those body parts with those AC fields can prevent metastases from growing in those body parts. This treatment may be used both after a metastasis has reached a detectable size and prophylactically (to prevent such metastases from ever reaching a detectable size in the first place). It may also be used to prevent cancer in people with a high probability of developing cancer (e.g., based on family history, encounter with radioactive materials, ingestion of carcinogens, etc.).

DETAILED DESCRIPTION OF PREFERRED EMBODIMENTS

Figure 1:
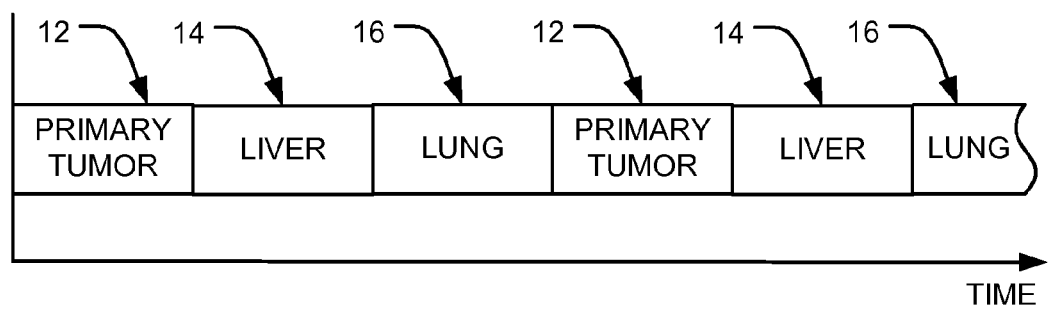
FIG. 1 is a timeline representation of the sequential application of TTFields to different regions of the body to prevent metastases.

The present invention relates to the treatment of two groups of potential patients: (1) patients suffering from cancer and (2) subjects at relatively high risk of developing cancer. For patients suffering from cancer, it is well known that in many cases the most severe complications and cause of death are the result of the severe effects of metastases. It is believed that metastases develop from tumor cells that escape from the primary tumor, penetrate the walls of blood or lymph vessels that grow into the tumor, flow with the fluid stream, exit the vessel at some remote location where they settle and proliferate to form new tumors. The liver and lung are the common locations to which metastases spread. To prevent the development of metastases is organs such as the lung and liver, TTFields are applied to these locations for the duration of the period when the formation of metastases is likely. This duration can span from a number of weeks to many months in the case of a person with a primary tumor that may spawn metastases. In the case of a person with a genetic propensity towards developing cancer, the treatment may be repeated at intervals that are appropriate for the type of cancer involved. For example, a course of treatment may be repeated every 6-12 months to destroy any cancer cells that may have developed before they get a chance to grow into a significant tumor.

The rationale behind the preventive tumor treatment is based on the following results obtained treating experimental animals with TTFields. A suspension of malignant melanoma tumor cells was injected intra-venous to two groups of mice. Such mice are known to develop numerous lung metastases. One group was subjected to TTFields at a frequency of 100 KHz and intensity of about 2 V/cm, with the field being applied in two different directions over the course of a 14 day period of treatment. The other group did not receive any treatment. The size and the number of lung metastases that were observed in the lungs of the treated group was dramatically lower than that of the untreated mice, as seen in Table 1 below. The differences between the Control and treated animals are statistically significant (Student t-test; $p<0.001$).

TABLE 1

|   | Average Lung Weight | Average Number of Tumors | Average Tumor Size (Diameter) |
| --- | --- | --- | --- |
| Treated | 212 ± 10 g | 1.5 ± 1 | 0.6 ± 0.3 mm |
| Control | 254 ± 20 g | 10.3 ± 8 | 1.9 ± 0.4 mm |

Another set of experiments was conducted in rabbits, inoculated under the kidney capsule, with a small V×2 tumor mass. One group of rabbits was treated by TTFields of corresponding parameters. The second group of rabbits with matching tumors did not receive any treatment. All the rabbits were sacrificed and their internal organs closely checked for metastases. The number of liver and lung metastases in the treated group was again dramatically lower than the corresponding numbers in the control group, as seen in Table 2 below. The control (untreated) lungs were almost completely covered by metastases, while only a few could be seen in the treated ones. The treated liver seemed free from metastases while large metastases could be seen in the non-treated liver.

TABLE 2

|   | Number of Large Metastases (>3 mm) | Total Number of Metastases |
| --- | --- | --- |
| Treated | 19 ± 14 | 72 ± 66 |
| Control | 41 ± 68 | 143 ± 134 |

In patients, in the present invention the preventive treatment is achieved by means of at least one set (pair) of electrodes, preferably two or more sets. The electrodes are connected to a waveform generator and amplifier so as to generate TTFields in the patient. Electrodes specifically designed for long term application without eliciting severe side effects and without causing patient discomfort and having minimal interference with the normal everyday activities of the patient are preferred. The placement of the electrodes is made so as to generate the desired field at the location or locations where the chances for tumor appearance are statistically high. In the case that a primary tumor is also present, the placement is preferably made so as to cover all tumors. Alternatively, for the presence, or projected presence of more than one tumor, additional sets of electrodes can be activated simultaneously. In such a case, it is preferable that the different sets of electrodes be connected to different generators which are isolated from one another. Isolation can be achieved by separate voltage sources (batteries) or, for example, by using isolation transformers.

FIG. 1 is a timeline of an alternative approach, in which the different sets of electrodes are positioned to treat different parts of the patient and are energized sequentially in a time-multiplexed manner. In the illustrated timeline, the primary tumor is treated in the first time slot 12 and the remote sites where metastases are likely to appear (e.g., the liver and lungs) are treated in the second and third time slots 14, 16, respectively. After all relevant regions have been treated, the three-part cycle is repeated. For example, the field could be applied to the primary tumor for one second, then to the liver for one second, then to lungs for one second, after which the three-part cycle is repeated for the desired period of treatment. Optionally, breaks may be included in the cycles of treatment. For example, the field could be applied to the primary tumor for 1-3 days, then to the liver for 1-3 days, then to the lungs for 1-3 days, then removed for 1-3 days, after which the four-part cycle is repeated for the desired period of treatment.

Since the various regions are treated sequentially when this approach is used, a single field generator can be used for all the sets of electrodes, and isolation transformers are not required. Optionally, the field may be applied in each time slot with a plurality of orientations and/or a plurality of frequencies, as described in U.S. patent application Ser. No. 11/111,439, filed Apr. 21, 2005, which is incorporated herein by reference.

Figure 2A:
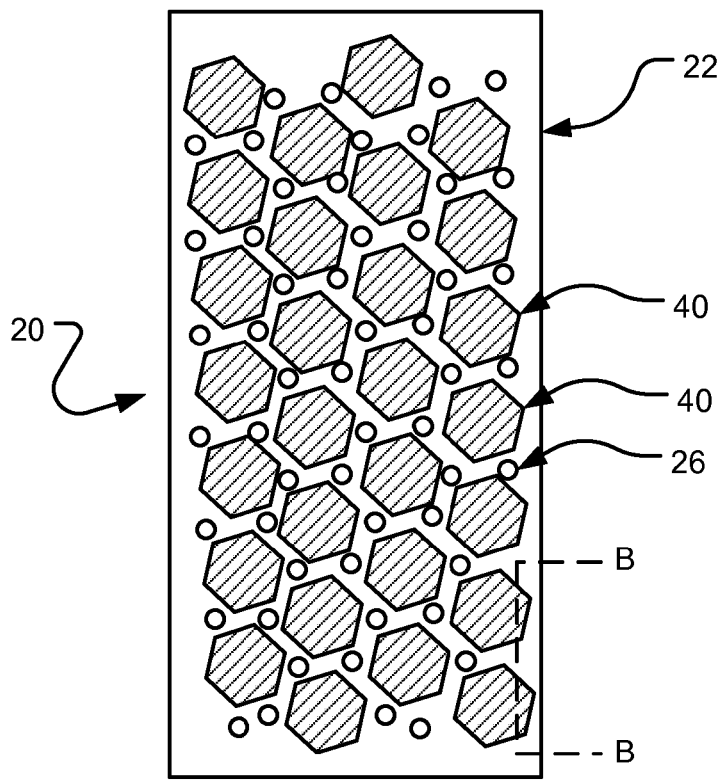
FIGS. 2a and 2b are schematic representations (in plan and section views, respectively) of flexible electrodes designed for long term application for the prevention of tumor development.
Figure 2B:
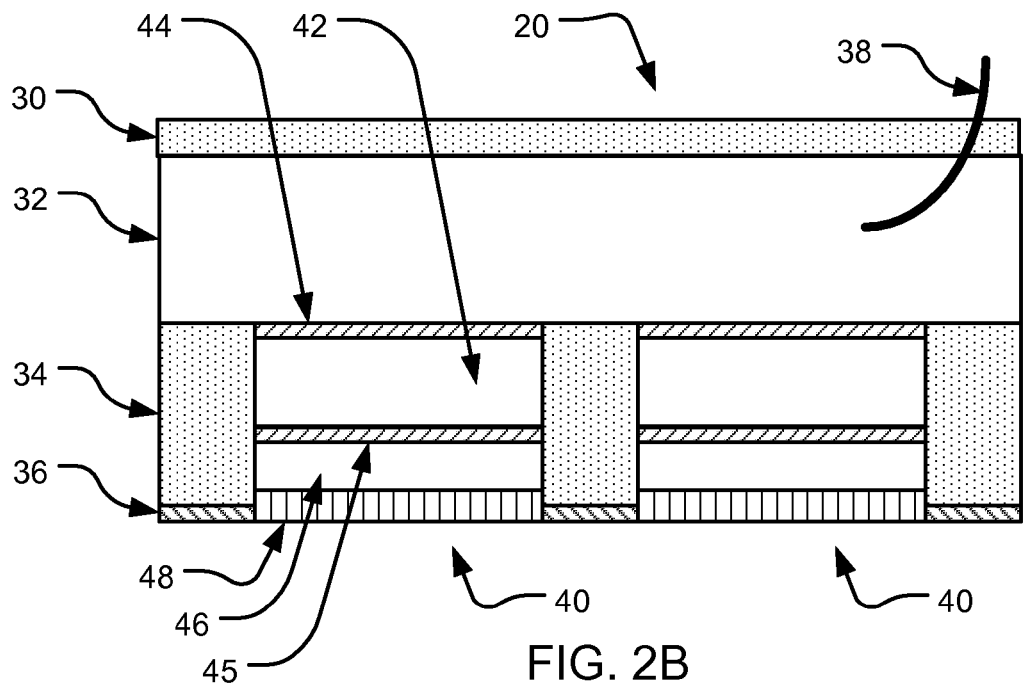

One example of a suitable electrode designed for comfortable long term use is shown in FIGS. 2a and 2b, with FIG. 2a being an plan view of a flexible electrode patch 20 and FIG. 2b being a detailed crossed section view the flexible electrode patch 20 along lines B-B. In this embodiment, the flexible electrode patch 20 is actually a composite of many small electrodes 40 that are mounted on a flexible substrate 22. The flexibility of the substrate 22 and the use of relatively small electrodes 40 helps provide flexibility, which allows the patch 20 to fit the relevant body curvature. Optionally, perforations 26 may be provided in the substrate to permit the skin beneath the substrate 22 to "breathe". In some embodiments, the material of the substrate 22 is selected so that it can be cut to a desired shape to fit the skin area to which the flexible patch 20 will be applied.

Depending on the location within the body that is being treated, one or more of the flexible electrode patches 20 would be used. For example, to treat a shallow melanoma, a single patch can be used, with the field being induced by applying an appropriate voltage between different electrodes 40 within the single patch 20. For deeper sites in the body, two or more patches 20 would preferably be placed on opposing sides of the site, and all the electrodes on any given patch would be wired together in parallel. An appropriate driving signal would then be applied between the various patches 20.

FIG. 2b shows a detailed cross-section of the flexible electrode patch 20 in which all the electrodes 40 on the patch are wired in parallel, depicted in cross-section. In this embodiment, the substrate is made of a preferably conductive flexible layer 32 mounted beneath a flexible insulating layer 30. Suitable materials for the conductive layer 32 include conductive rubber, graphite, thin flexible metal sheets such as copper or aluminum, etc.; and suitable materials for the flexible insulating layer 30 include rubber, silicon, Teflon and polyethylene vinyl. A lead 38 is wired in electrical contact with the conductive flexible layer 32 to facilitate application of the appropriate AC signals to each patch 20.

The cross-section view of FIG. 2b depicts electrodes 40 separated by insulators 34, which are preferably made of a flexible insulating material such as silicon rubber, vinyl, polyurethane, etc. In the illustrated embodiment, each electrode 40 includes conductive core 42 made of, for example, metal or conductive rubber, and a thin dielectric layer 46. Preferably, the dielectric layer is very thin (e.g., 0.1 mm) and has a very high dielectric constant (e.g., greater than 1000, or more preferably greater than 5000). Preferably, one layer of conductive adhesive 44 is provided between the core 42 and the conductive layer 32, and another layer of conductive adhesive 45 is provided between the core 42 and the dielectric layer 46.

Optionally, the portions of the insulator 34 that contact the patient's body may be coated with a biocompatible adhesive 36 to help the patch 20 adhere to the patient's body. A conductive layer 48 is preferably provided between the dielectric 46 and the patient's body to improve the electrical contact with the patient's body. Examples of suitable materials for this conductive layer 48 include conductive gels and carbon (graphite) powders, which maybe imbedded in a suitable cream (e.g. a cosmetic base with an electrolyte). Graphite has the advantage in that it has a much higher electric conductance, as compared with gels, and that it is inert and has extremely high biocompatibility. Optionally, a suitable adhesive may be included in the conductive layer 48 to help the patch 20 adhere to the patient's body. A number of alternative electrode configurations are described in U.S. patent application Ser. No. 11/294,780, filed Dec. 5, 2005, which is incorporated herein by reference.

The TTFields generated in the target regions are preferably in the order of 1-10 V/cm and the field frequency is preferably 100-300 kHz for certain types of cancers (e.g., certain gliomas and melanomas) and may be outside that range for other types of cancer, as described in the applications referenced above. The electrodes can be incorporated into articles of clothing so as to provide maximal comfort to the patient, as described in U.S. Pat. No. 6,868,289, which is also incorporated herein by reference.

Figure 3:
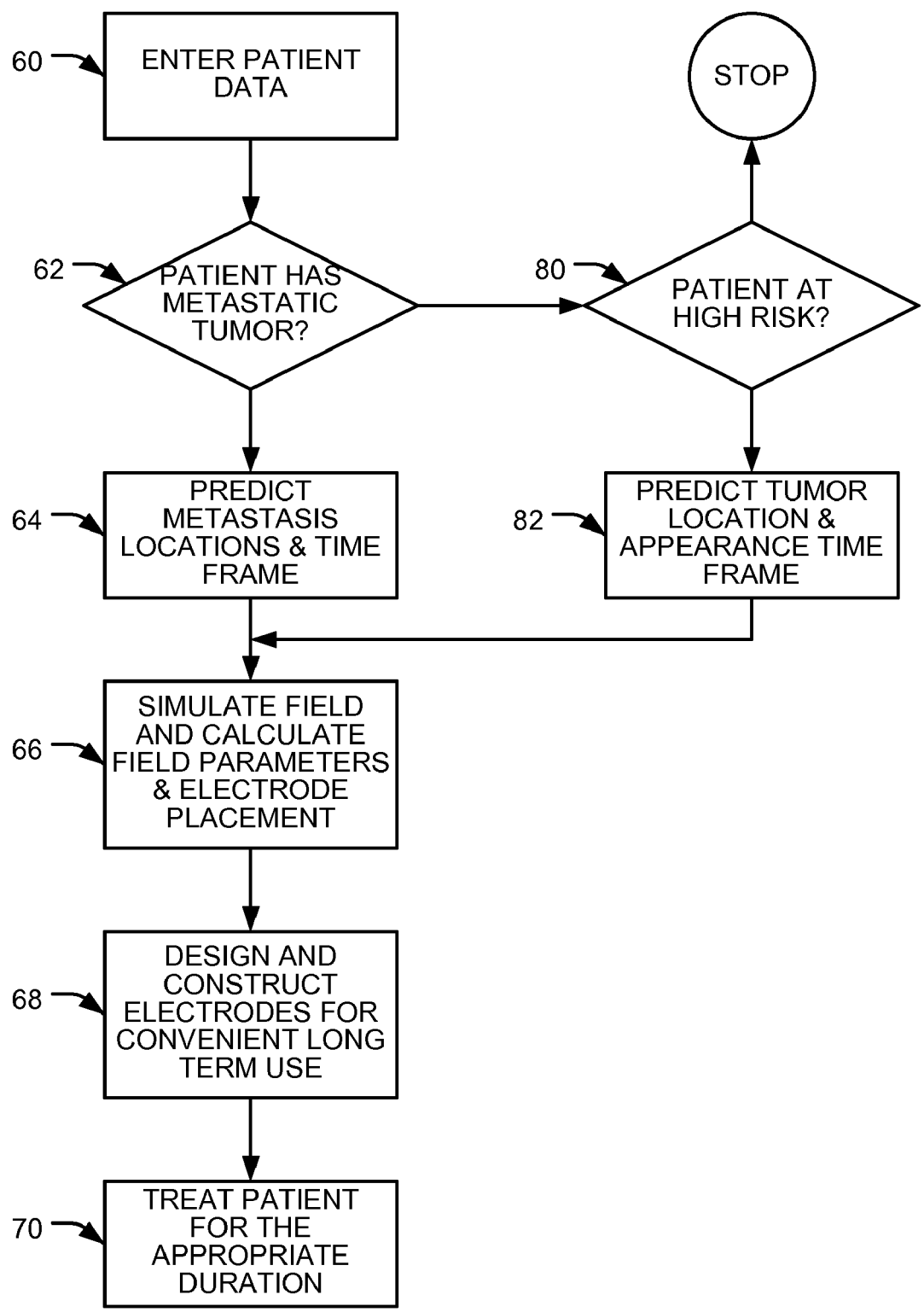
FIG. 3 is a process flowchart for the selection of patients for treatment and the preparation for initiation of treatment.

FIG. 3 is a flow chart of a process for using the above-described approaches to treat patients. The process begins in step 60, where information about the patient is obtained. This information should preferably include racial information and a family history that is sufficient to evaluate genetic risk of developing cancer, as well as personal history indicating whether the patient has or is suspected to have a tumor that may generate metastases.

In step 62, the process flow diverges depending on whether the patient is known to have a metastatic tumor. If the patient has a metastatic tumor, process flow continues at step 64, where the location or locations where metastases are expected to develop and the time frame when such metastasis may develop are determined. For example, metastases commonly develop in the lungs from certain types of melanomas, and in the liver, brain, or bone for certain other types of cancers. The process flow then continues in step 66, where the way to get the desired beneficial electrical fields to the locations identified in step 64 is computed (or, in alternative embodiments, estimated). This may be accomplished by running computer simulations to identify the type, size, and shape of the electrodes that should be used, the positions to place those electrodes, and the voltages that should be applied to those electrodes in order to induce the desired fields at the identified locations. The process flow then continues in step 68, where suitable electrodes for generating the desired fields are constructed. Finally, in step 70, the electrodes are applied to the patient's body and stimulated with appropriate voltages in order to generate the desired fields in the locations identified previously in step 64.

If, back in step 62, it turns out that the patient being evaluated does not have metastatic tumor, the process flow continues at step 80 where, based on the patient data that was entered in step 60, a determination is made as to whether the patient is at a high risk for developing cancer. If the patient's risk of developing cancer is not too high, the process stops (and the patient is not treated). If, on the other hand, it is determined that that patient's risk of developing cancer is sufficiently high, process flow continues at step 82, where the location or locations where cancer is likely to develop are determined. For example, patients with a strong family history of breast cancer or a genetic marker that is correlated with breast cancer, the determined location would be the breasts. The process then proceeds to step 66, and continues from there as described above.

Note that the above-described treatment may be advantageously combined with other cancer treatments such as surgery, chemotherapy, radiation therapy, etc. It may also be convenient to implement the above-described treatment using electrodes that are integrated into articles of clothing (e.g., a bra or a hat) as described in U.S. Pat. No. 6,868,289, which is incorporated herein by reference.

I claim:

1. A method of inhibiting the growth of metastases, the method comprising the step of:
    applying an alternating electric field to a location in a living body, wherein the electric field has frequency and field strength characteristics such that the electric field disrupts at least some cells as they undergo division while leaving non-dividing cells in the location substantially unharmed, and wherein the electric field is applied during one or more intervals of time that are cumulatively sufficient to inhibit growth of metastases in the location.

2. The method of claim 1, wherein the alternating electric field is applied to a location where metastases are likely to appear.

3. The method of claim 1, wherein the alternating electric field is applied to at least one of a liver, a lung, a brain, and a bone.

4. The method of claim 1, wherein the one or more intervals of time cumulatively comprise at least one week.

5. The method of claim 1, wherein the one or more intervals of time cumulatively comprise at least one month.

6. The method of claim 1, wherein the wherein the electric field has a frequency between about 100 kHz and about 300 kHz and a field strength between about 1 and about 10 V/cm.

7. A method of preventing metastases from growing, the method comprising the step of:
    applying an alternating electric field to a location in a living body, wherein the electric field has frequency and field strength characteristics that provide the electric field with the ability to prevent metastases from growing while leaving non-dividing cells in the location substantially unharmed, and wherein the electric field is applied during one or more intervals of time that are cumulatively sufficient to prevent the metastases from growing in the location.

8. The method of claim 7, wherein the alternating electric field is applied to a location where metastases are likely to appear.

9. The method of claim 7, wherein the alternating electric field is applied to at least one of a liver, a lung, a brain, and a bone.

10. The method of claim 7, wherein the one or more intervals of time cumulatively comprise at least one week.

11. The method of claim 7, wherein the one or more intervals of time cumulatively comprise at least one month.

12. The method of claim 7, wherein the wherein the electric field has a frequency between about 100 kHz and about 300 kHz and a field strength between about 1 and about 10 V/cm.

13. A method of inhibiting tumors from growing, the method comprising the steps of:
    determining a location in a patient's body where tumors are likely to appear;
    positioning electrodes with respect to the patient in positions that are selected to induce an alternating electric field at the location;
    applying a AC voltage across the electrodes that induces an electric field at the location, wherein the AC voltage and the electrodes have characteristics that result in the induced electric field having frequency and amplitude characteristics that disrupt cells that undergo division while leaving non-dividing cells in the location substantially unharmed, and
    wherein the electric field is applied for one or more periods of time that are cumulatively sufficient to inhibit growth of tumors in the location.

14. The method of claim 13, wherein the alternating electric field is applied to a location where metastases are likely to appear.

15. The method of claim 13, wherein the alternating electric field is applied to at least one of a liver, a lung, a brain, and a bone.

16. The method of claim 13, wherein the one or more intervals of time cumulatively comprise at least one week.

17. The method of claim 13, wherein the one or more intervals of time cumulatively comprise at least one month.

18. The method of claim 13, wherein the wherein the electric field has a frequency between about 100 kHz and about 300 kHz and a field strength between about 1 and about 10 V/cm.

19. A method of preventing tumors from growing, the method comprising the step of:
    applying an alternating electric field to a location in a living body, wherein the electric field has frequency and field strength characteristics such that the electric field disrupts a significant portion of cells as they undergo division while leaving non-dividing cells in the location substantially unharmed, and wherein the electric field is applied during one or more intervals of time that are cumulatively sufficient to disrupt a significant portion of cells in the location that undergo division; and repeating the applying step often enough to prevent tumors from growing in the location.

20. The method of claim 19, wherein the alternating electric field is applied to a location where metastases are likely to appear.

21. The method of claim 19, wherein the alternating electric field is applied to at least one of a liver, a lung, a brain, and a bone.

22. The method of claim 19, wherein the one or more intervals of time cumulatively comprise at least one week.

23. The method of claim 19, wherein the one or more intervals of time cumulatively comprise at least one month.

24. The method of claim 19, wherein the wherein the electric field has a frequency between about 100 kHz and about 300 kHz and a field strength between about 1 and about 10 V/cm.

25. The method of claim 19, wherein the repeating step comprises repeating the applying step at least once a year.

26. The method of claim 19, wherein the repeating step comprises repeating the applying step at least once every six months.

* * * * *